US008111836B1

(12) United States Patent
Graber

(10) Patent No.: US 8,111,836 B1
(45) Date of Patent: Feb. 7, 2012

(54) SYSTEM AND METHOD USING A PHASED ARRAY OF ACOUSTIC GENERATORS FOR PRODUCING AN ADAPTIVE NULL ZONE

(76) Inventor: Curtis E. Graber, Woodburn, IN (US)

( * ) Notice: Subject to any disclaimer, the term of this patent is extended or adjusted under 35 U.S.C. 154(b) by 1190 days.

(21) Appl. No.: 11/897,638

(22) Filed: Aug. 31, 2007

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 1/20*** | (2006.01) |
| ***H04R 1/02*** | (2006.01) |
| ***H04R 9/06*** | (2006.01) |
| ***H05K 5/00*** | (2006.01) |
| ***A47B 81/06*** | (2006.01) |

(52) U.S. Cl. .................... 381/71.7; 381/71.14; 381/350; 381/351; 381/336; 181/145; 181/199

(58) Field of Classification Search .................... 381/77, 381/82, 83, 93, 71.1, 71.7, 71.8, 71.14, 350, 381/351, 347, 349, 182, 160, 335, 336, 332; 181/199, 189, 144, 145, 147

See application file for complete search history.

(56) References Cited

U.S. PATENT DOCUMENTS

| | | | | |
|---|---|---|---|---|
| 5,713,916 | A | 2/1998 | Dias | |
| 5,715,319 | A | 2/1998 | Chu | |
| 5,813,998 | A | 9/1998 | Dias | |
| 5,894,288 | A | 4/1999 | Lee et al. | |
| 7,826,623 | B2 * | 11/2010 | Christoph | 381/92 |
| 2002/0091004 | A1 * | 7/2002 | Rackham | 472/60 |
| 2004/0062404 | A1 * | 4/2004 | Negishi et al. | 381/77 |
| 2007/0081680 | A1 * | 4/2007 | Yen | 381/182 |
| 2007/0223714 | A1 * | 9/2007 | Nishikawa | 381/71.1 |
| 2008/0174510 | A1 * | 7/2008 | Cassen et al. | 343/872 |
| 2010/0329480 | A1 * | 12/2010 | Boone | 381/94.1 |

* cited by examiner

*Primary Examiner* — Hai Phan

(74) *Attorney, Agent, or Firm* — Paul W. O'Malley; Susan L. Firestone

(57) ABSTRACT

A performance venue with a main speaker system is provided having a target coverage area within the performance venue. A performance area is located within the performance venue outside the target coverage area of the main speaker system. A low frequency directed audio source is positioned with respect to the performance area for active cancellation of low frequency sound spilling over into the performance area from the main speaker system. Control of the low frequency directed audio source is effected by an audio sensor is located in the performance area for generating an output correlated with low frequency spill over into the performance area.

6 Claims, 6 Drawing Sheets

SYSTEM AND METHOD USING A PHASED ARRAY OF ACOUSTIC GENERATORS FOR PRODUCING AN ADAPTIVE NULL ZONE

BACKGROUND OF THE INVENTION

1. Technical Field

The invention relates to active noise reduction and more particularly to suppression of low frequency spill over in a wide field, live performance type venue, through destructive interference of the spillover.

2. Description of the Problem

High fidelity sound systems for large auditorium and free field applications are readily made directional in the middle and upper frequencies. This helps direct sound energy toward the intended audience. However, most loudspeaker units perform increasingly as omnidirectional or monopole devices as the sound frequency reproduced decreases. This relatively difficult to direct low frequency, long wavelength sound energy can spill over into undesired areas, such as a stage set up in the field of view of the audience and on which an open microphone may be located. Where an open microphone is present spillover can lead to feedback, limiting the allowable gain from the microphone. On stage performers can find the spillover low frequency noise a distraction and highly misleading as to the character of the sound in the intended area of coverage.

Active sound cancellation is a developing field using destructive interference to produce a null sound field. The selective cancellation of low frequency sound would be made easier by availability of a directed beam low frequency device capable of relatively high levels of power output.

SUMMARY OF THE INVENTION

The invention provides an efficient, endfire array operating in conjunction with a conventional sound system to provide selective cancellation of spillover sound from the conventional sound system, particularly at frequencies where the conventional sound system functions as a monopole device. In a performance venue a main speaker system is provided having a target coverage area within the performance venue. A performance area is located within the performance venue outside the target coverage area of the main speaker system. A low frequency directed audio source is positioned with respect to the performance area for active cancellation of low frequency sound spilling over into the performance area from the main speaker system. An audio sensor is located in the performance area for generating an output correlated with low frequency spill over occurring with the performance area. A control system for the main speaker system and the low frequency directed audio source uses the output of the audio sensor as a control input.

Additional effects, features and advantages will be apparent in the written description that follows.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1A:
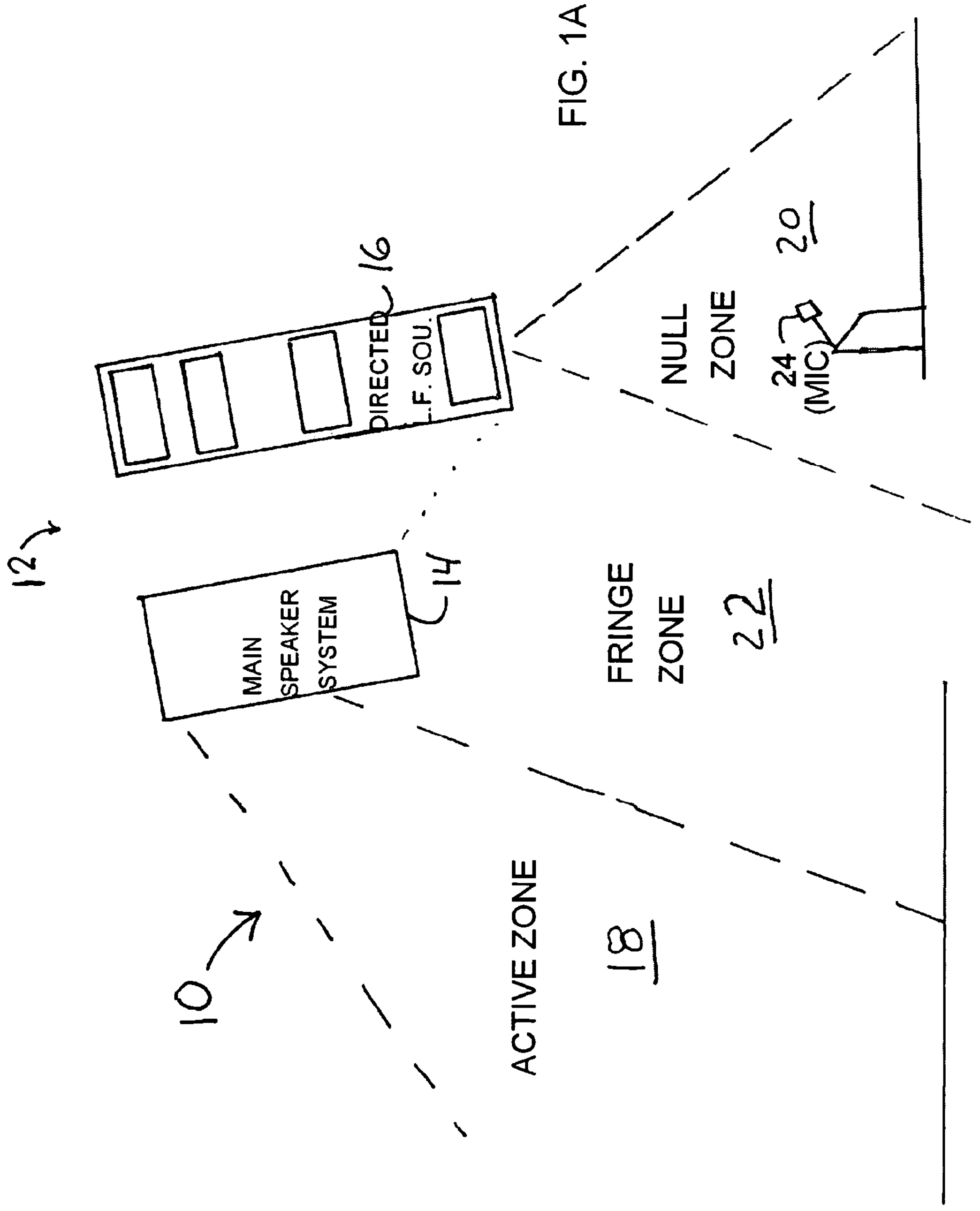
FIG. 1A is a side schematic of a performance venue constructed with the sound system of the present invention.
Figure 1B:
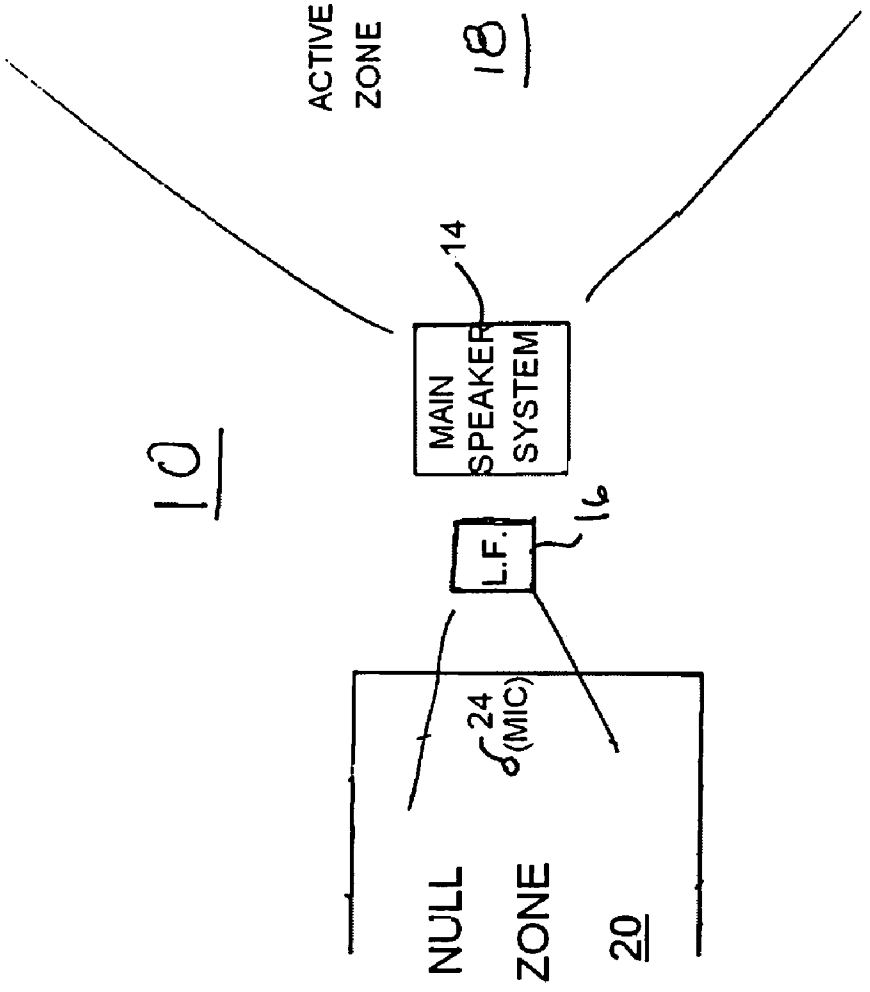
FIG. 1B is a top plan schematic of the performance venue of FIG. 1A.

Referring now to the figures and in particular to FIGS. 1A-B, there is illustrated a performance venue 10 having a sound system 12. Sound system 12 includes a main loudspeaker system 14 used for high fidelity sound reproduction and a directed low frequency audio source 16 used for selective, active cancellation of low frequency spillover from the main loud speaker system into a desired null zone 20.

Performance venue 10 is intended as a location where audiences gather for live performances. An active zone 18 for coverage by main loudspeaker system 14 intersects an audience seating area (not shown) from which the audience can observe performers located on a stage or similar performing area corresponding to the null zone 20. The oral and instrumental parts of performances within the null zone 20 are intended to be picked up using microphones, including what is termed here as an audio sensor 24, amplified and directed into the audience over main speaker system 14. In order to allow maximum gain to be applied to the sound pick up in the null zone 20 it is undesirable that sound from the main speaker system 14 be audible in the null zone 20, since doing so could result in undesirable feedback and further because the inherent delay would be disruptive to many types of performances, particularly performances of contemporary music.

Ideally main speaker system 14 is highly directional, with a generated sound field corresponding to the active zone 18. In actual application the coverage of an "active zone" is frequency dependent and tends to spread uncontrollably from conventional speaker arrays at the lowest frequencies (particularly below 250 HZ where most speaker systems become monopoles, that is, undirected). Thus, while for some performances a null zone 20 may be a natural result of the directionality of the main speaker system 14, for other performances, particularly those with a strong bass component, the null zone may have to be generated, for example by physical variation of the performance venue 10, or the gain of the microphones 24 limited. Of course, it is not always possible to control the physical aspects of the performance venue 10, particularly if sight lines are to be kept open. Selective active sound cancellation is used in the present invention to produce a null zone 20 of selected size at the desired location. The present invention uses a directed low frequency sound source 16 to effect cancellation of spillover low frequency sound from the main speaker system 14 to produce the null zone 20. A consequence of using active cancellation is an intermediary fringe zone 22 between the null zone 24 and the active zone 18. The depiction of the fringe zone 22 is not intended to suggest that its existence is desirable, just that it is a byproduct of the process described here.

In order to produce a null zone 20 of a desired size and location it is highly beneficial to have a directed low frequency sound source 16. Such is provided here by an endfire array of woofers as described below.

Figure 2:
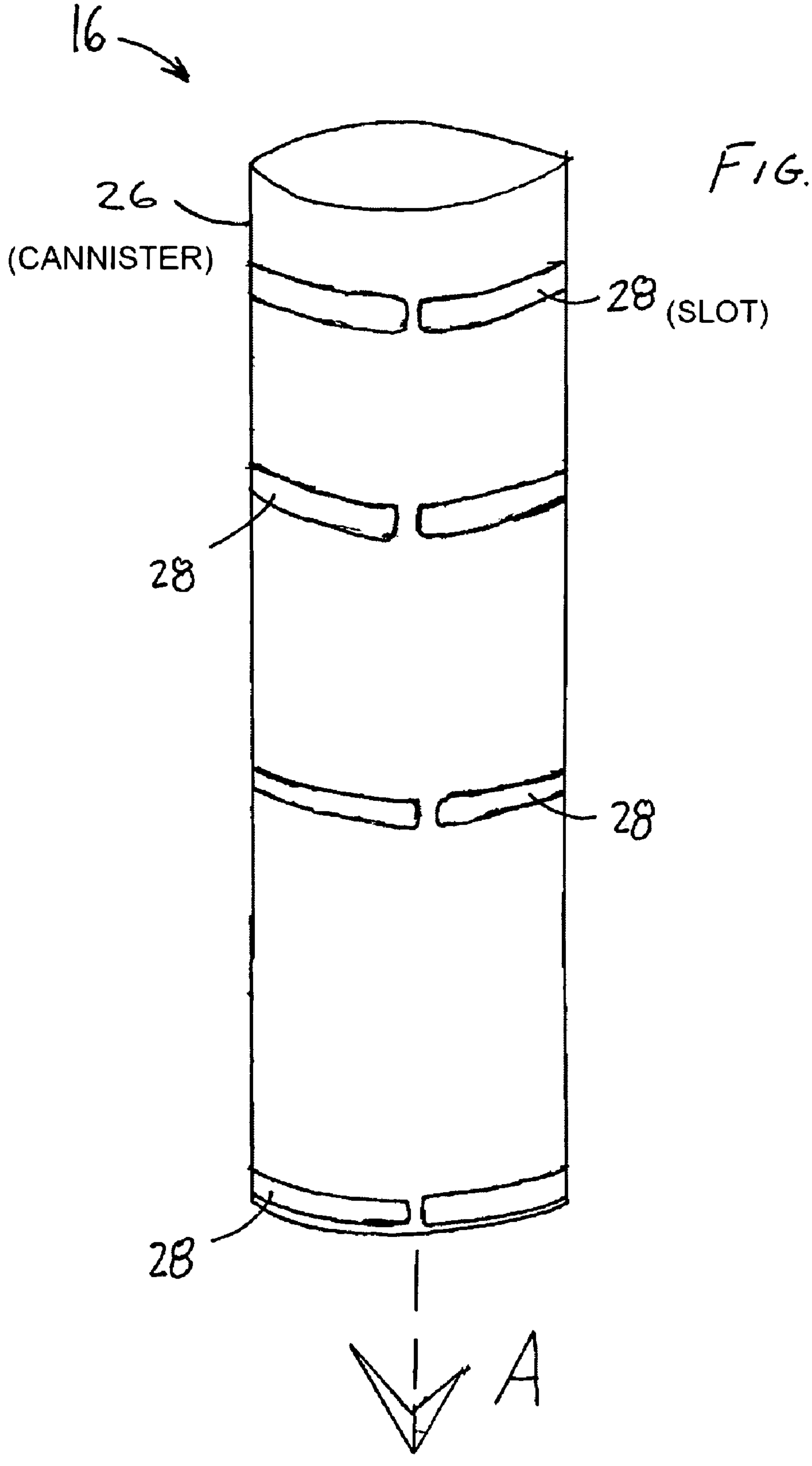
FIG. 2 is a perspective view of an endfire bass loud speaker array.

FIG. 2 illustrates a directed low frequency sound source 16 which generates a sound field which is strongest centered on a primary propagation axis A extending from one end of the device. Sound source 16 comprises a cannister 26 which houses the woofer array of the source. Sound is emitted from circumferential slots 28 located spaced from one another at locations along the primary propagation axis A. In a preferred embodiment the spacing between slots 28 increases from one to the next along the primary propagation axis A.

Figure 3:
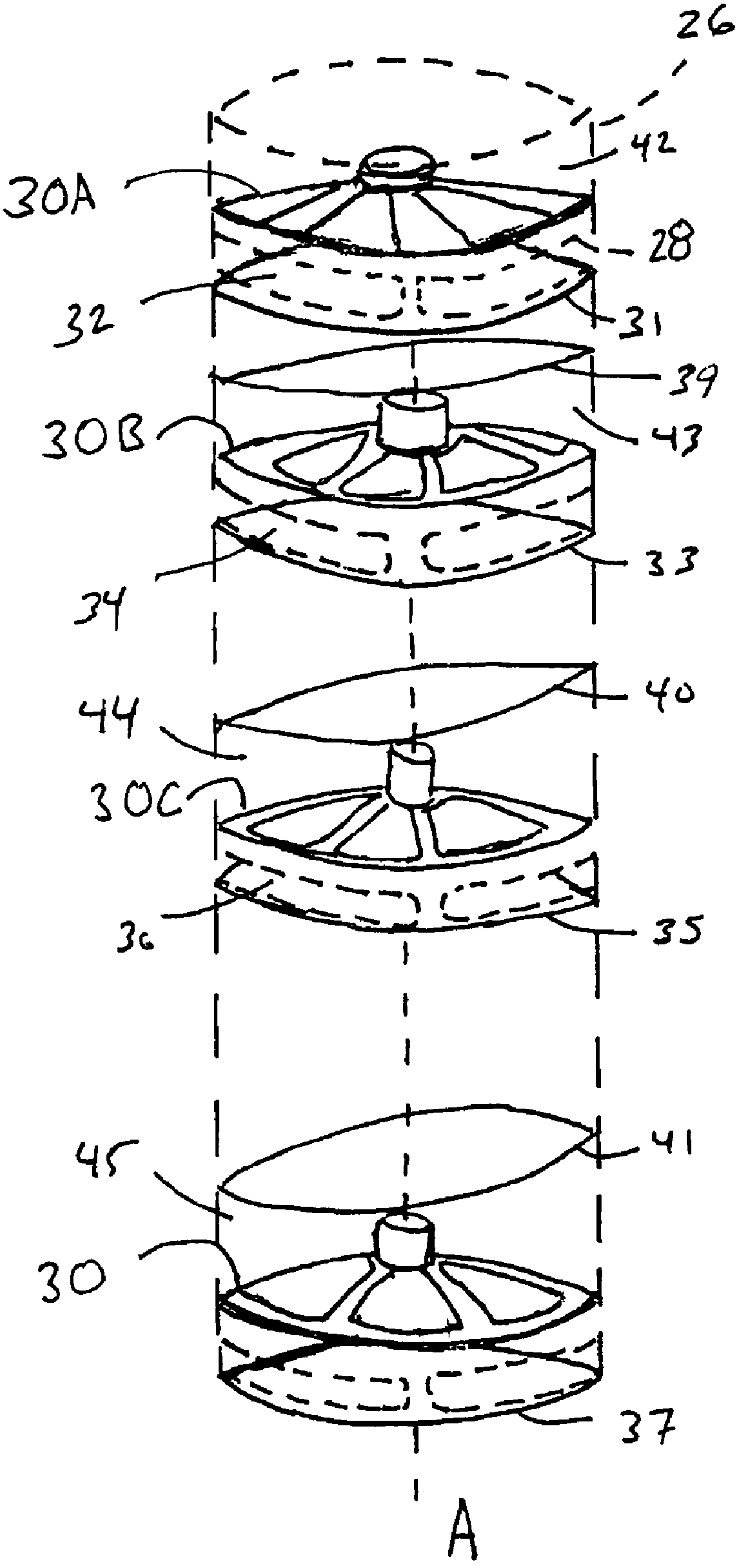
FIG. 3 is a cutaway view of the endfire bass loud speaker array of FIG. 2.

FIG. 3 illustrates the internal arrangement of an exemplary directed low frequency sound source 16. A stack of four woofers 30A-D, all centered on and aimed along the primary axis A of sound propagation are provided. Woofers 30A-D are preferably progressively spaced in the primary direction of sound propagation. If the spacing between woofers 30A and 30B is "x", than the spacing between woofers 30B and 30C is "2x" and between 30C and 30D is "3x". Each woofer 30A-D is located to radiate between a sealed backchamber (42, 43, 44, 45) and a front chamber (32, 34, 36, 38). Appropriate internal baffles (31, 33, 35, 37, 39, 40 and 41) are provided to form walls of the back and front chambers so that the backchambers are equal in size to one another and the front chambers are equal in size to one another. Slots 28 from the front chambers should no more than half the size in area as the diaphragm of the respective woofers 30A-D. This achieves compression throat loading improving device efficiency. The longer the array can be made, preferably by inclusion of ever greater numbers of woofers, effects ever longer frequencies of sound which can be actively cancelled. The total length of the device (i.e. the distance separating the first and last woofers in an array) defines the lowest frequency which can be cancelled.

Figure 4:
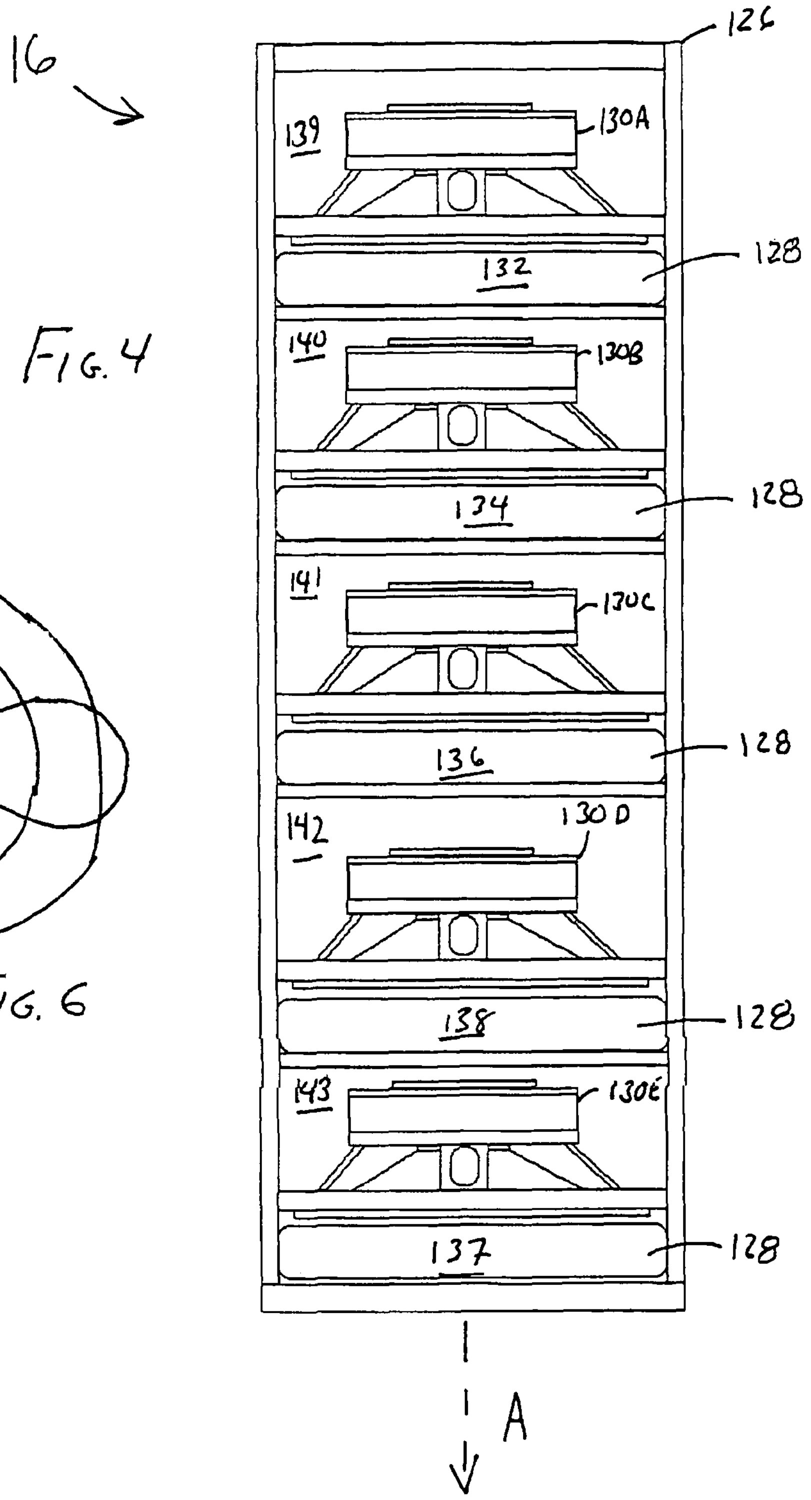
FIG. 4 is a cross sectional view of an endfire loudspeaker array usable in the invention.

It is not essential that the spacing between adjacent woofers be increased with each successive woofer moving in the direction of intended primary radiation. FIG. 4 illustrates a directed low frequency sound source 16 in which the spacing between adjacent woofers 130A-E is equidistant. Slots 128 are equidistantly spaced, but otherwise the device is essentially similar to the device of FIG. 3, incorporating sealed back chambers 139, 140, 141, 142 and 143, and front chambers 132, 134, 136, 138 and 137. Performance for array 126 for a unit of identical length using increasing spacing between loudspeakers is somewhat improved, but at the expense of including a larger number of loudspeakers.

The back chambers of either device are sealed but tuned via volume and free air resonance to the driver. The front chambers are also tuned via volume, but ported by the slots. It is expected that the end fire arrays, mounted in cylinders, would be built with 4 to 8 inch diameter cone transducers, though any conventional acoustic transducer could be used. An effective bandwidth from 40 HZ to 1 KHZ is anticipated. Substantial feedback rejection is anticipated.

Figure 6:
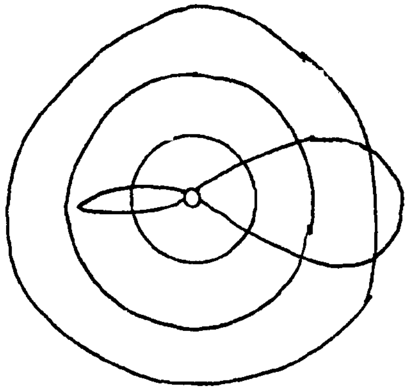
FIG. 6 is a polar graph of the sound field generated by the directed low frequency audio source used in the loudspeaker system of the invention.

FIG. 6 illustrates an ideal two lobed sound field produced by an endfire array of woofers with a deeper, wider array being propagated in forward direction, and a narrow, shallow lobe in the reverse direction. Where the array is flown in a hall it is expected that the reverse lobe will be directed into the ceiling.

Figure 5:
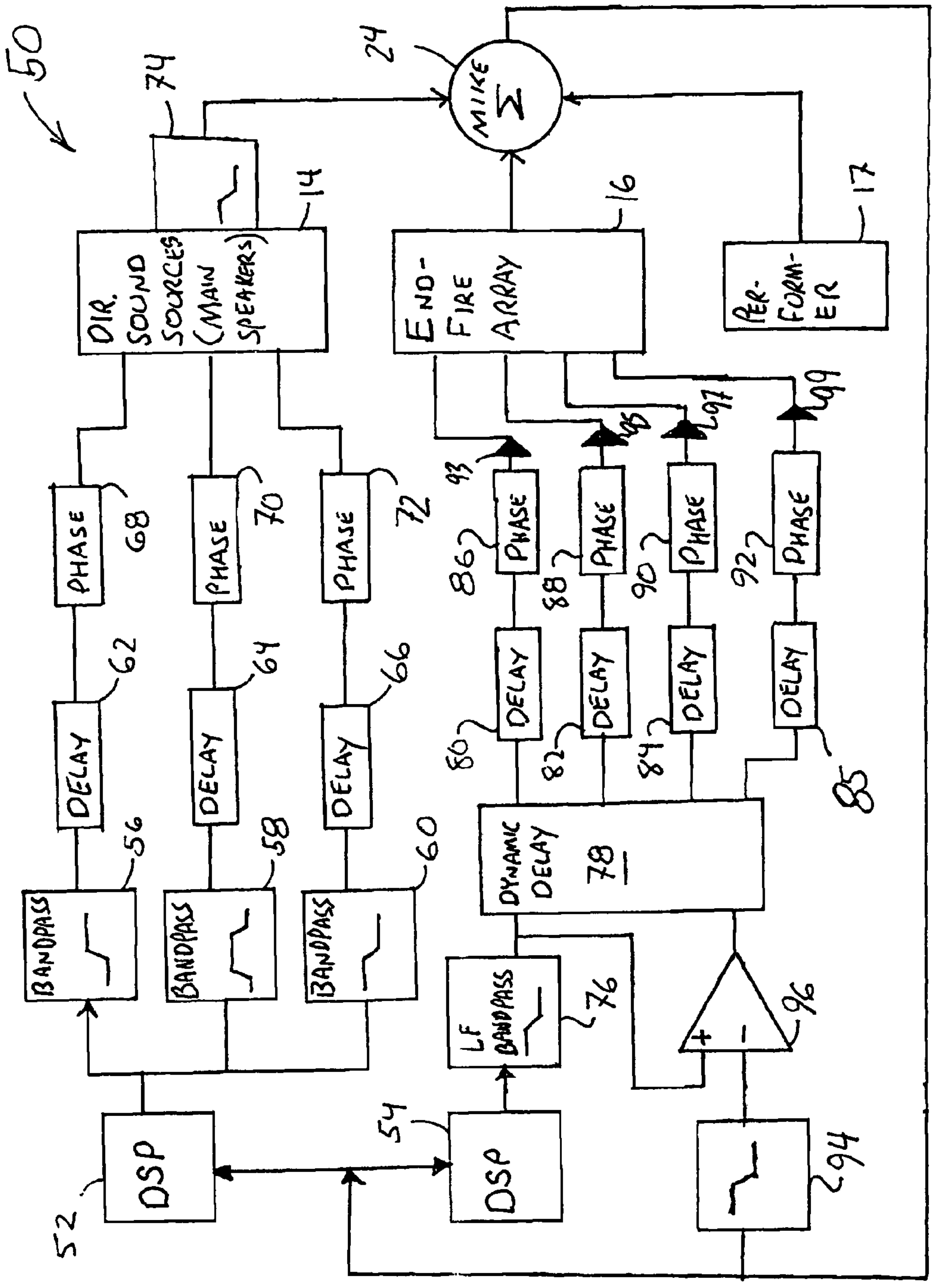
FIG. 5 is a block diagram schematic of the control system for the loudspeaker system of the invention.

FIG. 5 is a block diagram of a control system 50 for a sound system 10. Control system 50 includes inputs from a performer(s) 17 and feedback from both the endfire array 16 and the main speaker system 14, all shown as directed through a microphone (mike/sound sensor) 24. The output of microphone 24 is coupled back to a main channel digital signal processor (DSP) 52 and a cancellation channel digital signal processor (DSP) 54. DSP 52 provides audio engineering control of mix and gain for optimal propagation of the sound in a venue based on venue parameters and possibly variables such as audience size.

The main channel of the sound amplification and reproduction from DSP 52 to the main speakers 14 is completely conventional and is depicted at a high level. The sound is divided into three bands (high, middle and low) by applying the signal to appropriate band pass filtering stages 56, 58 and 60. The output of the high frequency band pass stage 56 is applied to delay and phase adjustment stages 62 and 68 (and possibly an amplification stage, not shown) before application to appropriate drivers in the main speaker system 14. The output of the high frequency band pass stage 56 is applied to delay and phase adjustment stages 62 and 68 (and possibly an amplification stage, not shown) before application to appropriate drivers in the main speaker system 14. The output of the medium frequency band pass stage 58 is applied to delay and phase adjustment stages 64 and 70 (and possibly an amplification stage, not shown) before application to appropriate drivers in the main speaker system 14. The output of the low frequency band pass stage 60 is applied to delay and phase adjustment stages 66 and 72 (and possibly an amplification stage, not shown) before application to appropriate drivers in the main speaker system 14. A low pass filter 74 is illustrated as interposed between the main speakers 14 and microphone 24. This is not intended to imply that an electronic circuit element is located here, but to reflect the physical effects of location of the microphone/audio sensor 24 outside the main coverage zone of the main speakers 14 but in a low frequency spill over area relative to the main speakers 14.

The drive circuitry for the end fire array/LF directional sound source 16 is essentially the same as that for the main speakers 14 except that a dynamic delay stage 78 is applied to the drive signal. The delay is varied on the basis of a difference signal generated by a differential amplifier 96, which compares the low frequency components of the processed drive signal from DSP 54 and LF bandpass filter 76 and the output of a low frequency band pass filter 94 taken directly from the output of microphone 24. In other words the dynamic delay stage 78 introduces a delay based on what is occurring on stage and what is input to the main channel. A distinct drive signal is produced for each driver of the end fire array 16. These signals have a fixed delay and phase adjustment (delay stages 80, 82, 84 and 85, phase adjustment stages 86, 88, 90 and 92) relative to one another based on the physical parameters of the end fire array 16. End stage amplification (stages 93, 95, 97, 99) is provided as required by the venue (e.g. distance from the stage).

The invention provides active noise cancellation for selected zones of a performance venue, typically the stage areas, where the potential for feedback is strong and the possibility of disruption of the performance is strong.

While the invention is shown in only one of its forms, it is not thus limited but is susceptible to various changes and modifications without departing from the spirit and scope of the invention.

What is claimed is:

1. A performance venue comprising:

a defined area for locating an audience and performers;

a main speaker system having an active zone within the defined area;

a performance area within the defined area which is located outside the active zone;

a low frequency directed audio source comprising a plurality of low frequency cone loudspeakers disposed for operation as an endfire array positioned and oriented for projecting sound into the performance area concurrently with operation of the main speaker system for cancellation of low frequency sound spilling over into the performance area from the main speaker system to produce a null zone within the performance area at a selected location and of a selected size, the endfire array having an enclosure extended in the direction of an intended axis of sound propagation with the enclosure having a central axis aligned with intended axis of sound propagation and the plurality of cone loudspeakers being disposed in the enclosure and centered on the central axis, the cone loudspeakers being located in the enclosure to have sealed back chambers and ported front chambers;

an audio sensor located in the performance area for generating an output; and a control system for the main speaker system and the low frequency directed audio source using the output of the audio sensor as a control input for determining a dynamic delay for the low frequency directed audio source.

2. A performance venue according to claim 1, wherein the endfire array further comprising:

slots from the respective front chambers being equidistantly spaced from adjacent slots in direction of elongation.

3. A performance venue according to claim 1, wherein the endfire array further comprising:

slots from the respective front chambers exhibiting increasing spacing between adjacent slots in the direction of primary sound propagation.

4. A sound system comprising:

a main speaker system having an active zone;

a performance area located outside the active zone of the main speaker system but open thereto;

an endfire array having a plurality of low frequency cone loudspeakers, the endfire array being positioned to direct sound into the performance area for active cancellation of low frequency sound generated by the main speaker system spilling over into the performance area from the active zone at a selected location and over a selected area;

the endfire array comprising an enclosure extended in the direction of an intended axis of sound propagation, the enclosure having a central axis aligned with intended axis of sound propagation;

the plurality of cone loudspeakers disposed in the enclosure and centered on the central axis, the cone loudspeakers being located in the enclosure to have sealed back chambers and ported front chambers;

an audio sensor located in the performance area for generating an output; and a control system for the main speaker system and the low frequency directed audio source using the output of the audio sensor as a control input for delay control over the low frequency directed audio source.

5. A sound system according to claim 4, wherein the endfire array further comprising:

slots from the respective front chambers being equidistantly spaced from adjacent slots in direction of elongation.

6. A sound system according to claim 4, wherein the endfire array further comprising:

slots from the respective front chambers exhibiting increasing spacing between adjacent slots in the direction of primary sound propagation.

* * * * *